United States Patent [19]

Kunz et al.

[11] Patent Number: 5,262,034
[45] Date of Patent: Nov. 16, 1993

[54] ELECTROCHEMICAL SENSOR FOR MONITORING ELECTROCHEMICAL POTENTIALS OF FUEL CELL COMPONENTS

[75] Inventors: Harold R. Kunz, Vernon; Richard D. Breault, Coventry, both of Conn.

[73] Assignee: International Fuel Cells Corporation, South Windsor, Conn.

[21] Appl. No.: 966,002

[22] Filed: Oct. 23, 1992

[51] Int. Cl.$^5$ .............................................. G01N 27/26
[52] U.S. Cl. ................................. 204/401; 204/400; 204/153.1
[58] Field of Search .................... 204/153.1, 400, 401; 429/14, 90

[56] References Cited
U.S. PATENT DOCUMENTS 4,500,391 2/1985 Schmidt et al. .................. 204/153.1
5,059,290 10/1991 Uchiyama et al. ............... 204/153.1

Primary Examiner—John Niebling
Assistant Examiner—Bruce F. Bell
Attorney, Agent, or Firm—Pamela J. Curbelo

[57] ABSTRACT

An electrochemical sensor comprised of wires, a sheath, and a conduit can be utilized to monitor fuel cell component electric potentials during fuel cell shut down or steady state. The electrochemical sensor contacts an electrolyte reservoir plate such that the conduit wicks electrolyte through capillary action to the wires to provide water necessary for the electrolysis reaction which occurs thereon. A voltage is applied across the wires of the electrochemical sensor until hydrogen evolution occurs at the surface of one of the wires, thereby forming a hydrogen reference electrode. The voltage of the fuel cell component is then determined with relation to the hydrogen reference electrode.

5 Claims, 2 Drawing Sheets

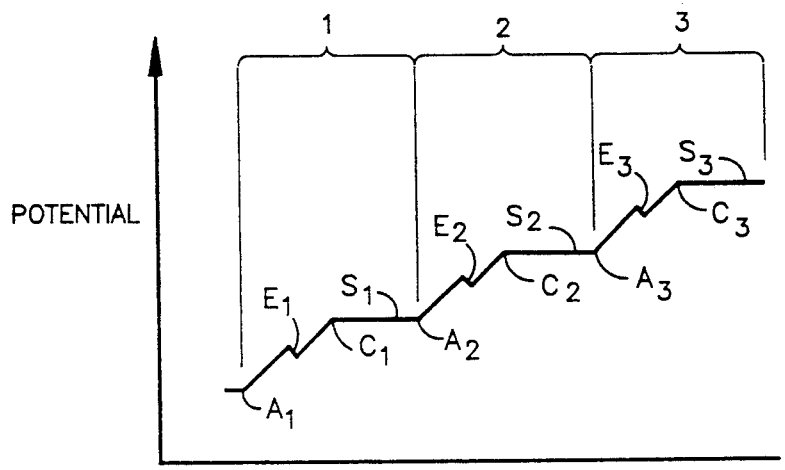
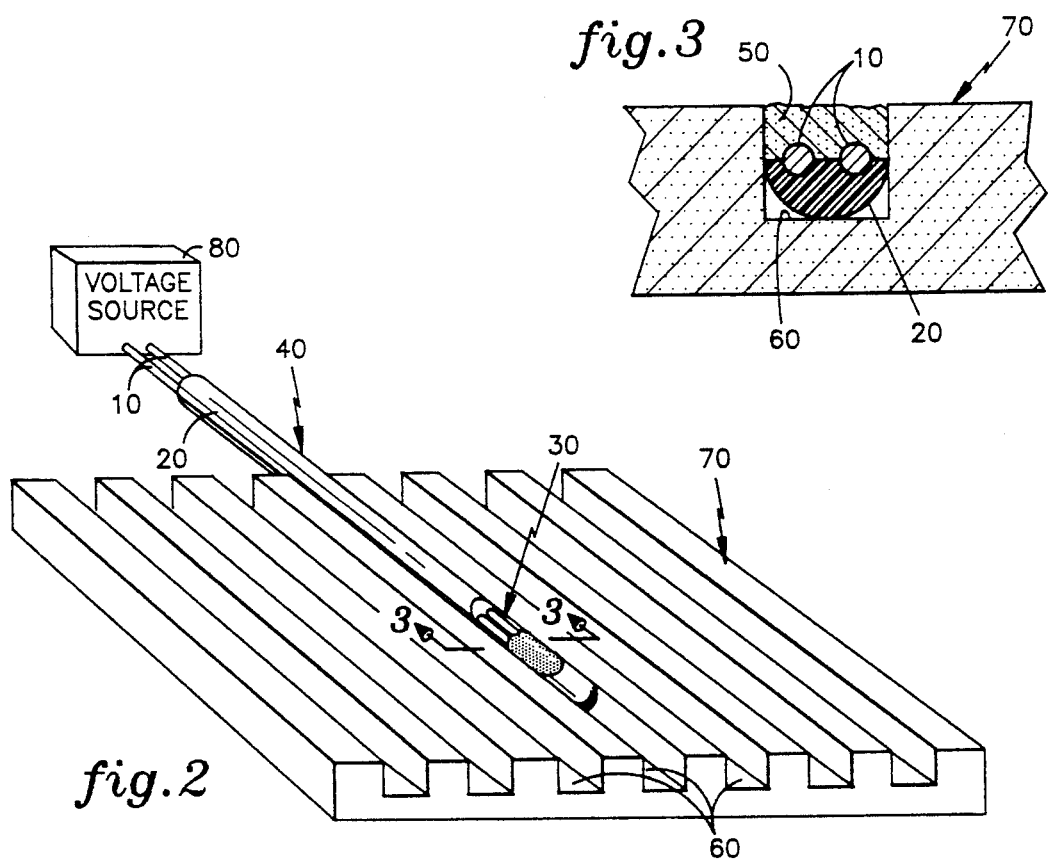

ELECTROCHEMICAL SENSOR FOR MONITORING ELECTROCHEMICAL POTENTIALS OF FUEL CELL COMPONENTS

The government has rights in this invention pursuant to a contract awarded by the Department of Energy.

CROSS REFERENCE TO RELATED APPLICATION

Reference is hereby made to commonly owned U.S. patent application Ser. No. 07/965,312, which discloses subject matter related to the subject matter of the present application.

TECHNICAL FIELD

The present invention relates to an electrochemical sensor, and especially to an electrochemical sensor for monitoring electric potentials of fuel cell components.

BACKGROUND OF THE INVENTION

Many fuel cells used in the production of electricity contain, sequentially, an electrolyte reservoir plate, an anode chamber, an anode electrode, an electrolyte, a cathode electrode, a cathode chamber, a second electrolyte reservoir plate, and a separator plate. Several of these fuel cells are aligned in electrical series to form a fuel cell stack capable of producing electricity.

During operation of the fuel cell stack, electric potentials are created across individual fuel cells and across the stack itself. These potentials are illustrated in FIG. 1 where the electric potential increases from the anode of cell 1 ($A_1$) to the electrolyte at the anode of cell 1, decreases through the electrolyte of cell 1 ($E_1$) between the anode and cathode, and then again increases to the cathode of cell 1 ($C_1$). The potential then remains virtually constant from cell 1 to cell 2 across the cell 1 separator plate ($S_1$) Then, again, cell 2's potential increases from the anode ($A_2$) to the cathode ($C_2$). This sequence continues through the fuel cell stack to the end cell. Even though, as can be seen at $E_1$, $E_2$, and $E_3$, there is a slight decrease in potential across the electrolyte of each cell, the overall potential of an individual cell increases from the anode to the cathode. Similar electric potential differentials exist across the various fuel cell components during fuel cell shutdown.

Since high potentials, greater than about 0.9 volts (with respect to a hydrogen electrode), may cause electrode corrosion, while low potentials, less than about 0.1 volt, may damage the cathode catalyst, knowledge of these potentials can be utilized to limit or prevent corrosion and damage of the electrodes by establishing procedures to reduce the electric potentials thereof to a safe level. Therefore, what is needed in the art is a means for determining the electrochemical potential of the various fuel cell components.

DISCLOSURE OF THE INVENTION

The present invention relates to a method for monitoring electrochemical potentials of components in a fuel cell. This method utilizes an electrochemical sensor which has a first electrically conductive wire and a second electrically conductive wire and a porous, non-conductive conduit in contact with the first wire and the second wire. The conduit contacts an electrolyte which is wicked into the pores of the conduit, a voltage is applied across the first wire and second wire, and the voltage is increased until hydrogen evolves from the second wire. A reading of the potential difference between the fuel cell component and the second wire is taken.

The foregoing and other features and advantages of the present invention will become more apparent from the following description and accompanying drawings.

BRIEF DESCRIPTION OF THE DRAWINGS

FIG. 1 is a graph representing the potential profile across a fuel cell stack and the individual fuel cells located therein.

FIG. 2 is a schematic of one embodiment of the electrochemical sensor of the present invention located in a groove of a fuel cell electrolyte reservoir plate.

FIG. 3 is a cross-sectional view of the electrochemical sensor of FIG. 2.

Figure 4:
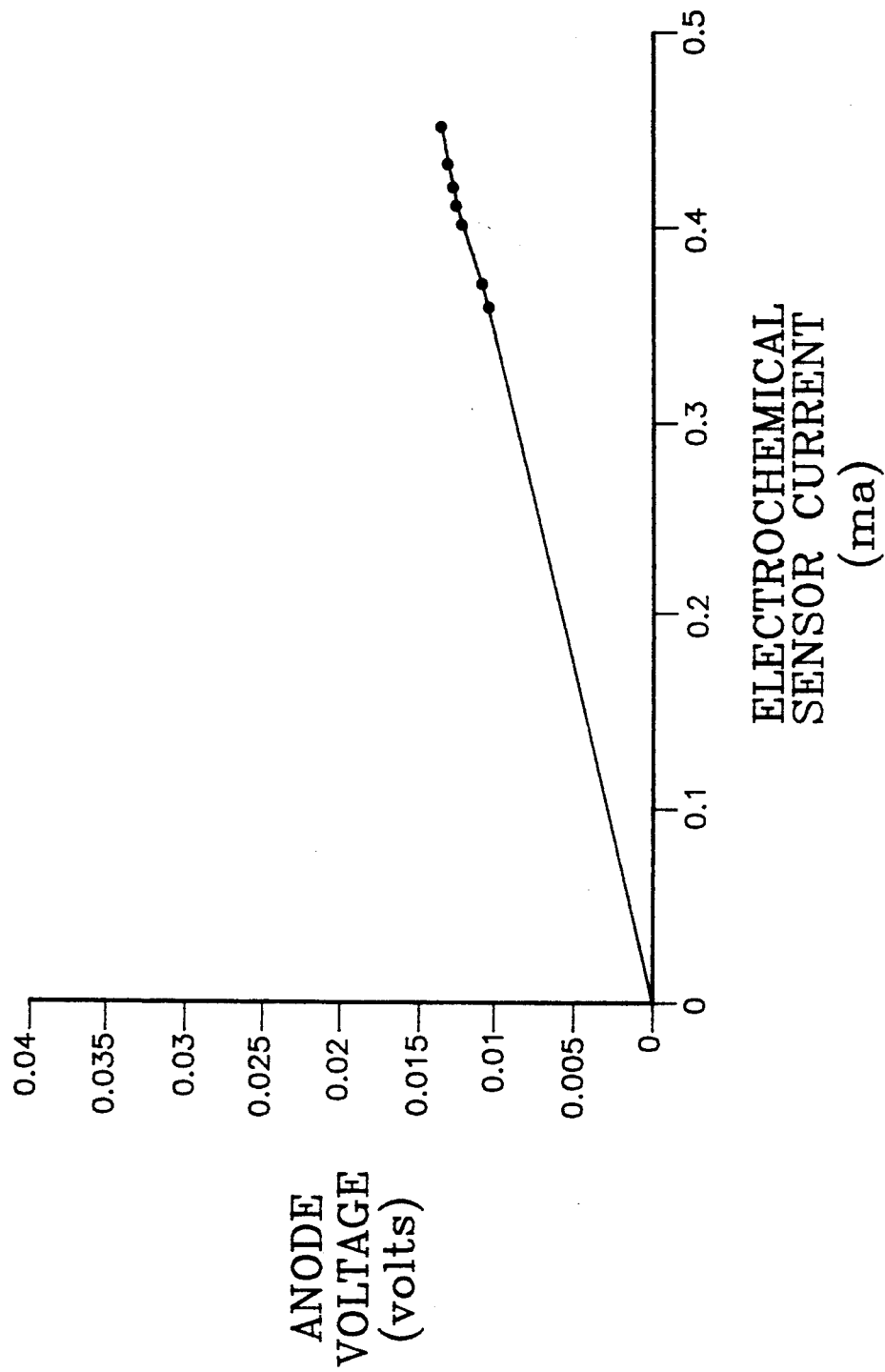
FIG. 4 is a graph of the anode electrode voltage during shut-down as determined using the electrochemical sensor as a reference electrode.

These FIGURES are meant to more clearly explain the present invention and not to limit the scope thereof.

BEST MODE FOR CARRYING OUT THE INVENTION

Referring to FIGS. 2 and 3, the electrochemical sensor 40 of the present invention comprises a pair of electrically conductive wires 10 substantially encapsulated within an electrically non-conductive sheath 20 with an electrically non-conductive conduit 50 located in an opening 30 in the sheath 20 to provide a medium for electrolyte to flow from an electrolyte reservoir plate 70 to the wires 10. This electrolyte reservoir plate 70 can be any conventional electrolyte containing body.

The wires 10 are conventional wires which are capable of conducting electricity an compatible with the fuel cell environment. Since the electrochemical sensor 40 operates similar to a hydrogen reference electrode where hydrogen is evolved on the surface of one of the wires through a water electrolysis reaction occurring on the wires 10, these wires 10 should be catalytically active, either inherently or the surface of the wires can be catalyzed by conventional means such as platinization, coating, or the use of a catalyzed rolled screen positioned around and in contact with the wires 10. Some possible wires 10 include noble metal based Wires and noble metal alloy wires such as gold based, iridium based, palladium based, platinum based, ruthenium based, rubidium based, rhodium based, alloys thereof, and others. The size of these wires 10 is dependent upon the specific application and is readily determined by an artisan. For example, in a phosphoric acid fuel cell, the electrochemical sensor typically occupies an about 1.6 millimeters (mm) wide groove in the electrolyte reservoir plate. As a result, about 0.2 mm to about 0.5 mm constitutes the preferred wire diameter, with about 0.35 mm to about 0.40 mm especially preferred.

In order for the wires 10 to function as a hydrogen reference electrode, a voltage must be applied across the wires such that a direct electrical current flows from the second wire through the electrolyte to the first wire, thereby providing the necessary electrons to electrolyze water in the electrolyte to form hydrogen ions, electrons, and oxygen gas. Essentially, water at the first wire is oxidized to oxygen gas, hydrogen ions, and free electrons. The hydrogen ions migrate to the second wire where they react with free electrons which have passed from the first wire, through the direct current supply, to the second wire, to produce hydrogen gas.

The voltage required to produce the direct electric current for this electrolysis can be determined by graphing the voltage difference between the second wire of the sensor and the fuel cell anode electrode versus the voltage applied across the two wires of the electrochemical sensor which causes electrons to flow from the second wire through the electrolyte to the first wire. Once the electrochemical sensor attains water electrolysis and therefore hydrogen evolution, the graph of the voltage potential versus the voltage applied to the electrochemical sensor will become nearly constant. This constant voltage, which indicates that sufficient hydrogen is being generated at the second wire of the electrochemical sensor to provide a hydrogen reference electrode which is near the open circuit potential of a hydrogen reference electrode, constitutes the base reading. Typically, this base reading exceeds about 0.8 volts and often lies in the range of about 1.35 volts to about 2.1 volts.

With the base reading, the electrochemical potential of various components within the fuel cell can be determined using the second wire (electrochemical sensor cathode) and a volt meter or other conventional device for measuring voltage. The volt meter (not shown) is connected to both the second wire and the fuel cell component to be monitored, a voltage is applied across the first wire and the second wire at the base reading voltage, and voltage between the component and the second wire is measured. This voltage reading, which can be up to about 1.2 volts, provides the component's electric potential relative to a hydrogen electrode. For example, an anode electrode potential during shut down is graphed according to the information obtained utilizing the electrochemical sensor of the present invention as described above. (See FIG. 4). The anode electrode potential equalled about 0.012 volts, relative to the reference potential, and therefore was below the 0.9 volts which can cause electrode damage.

Establishment of the hydrogen reference electrode relies upon water electrolysis and the flow of electrons. In order to preserve the circuit between the wires 10, the wires 10 must be prevented from physically contacting one another. Therefore, sufficient space to enable current flow and to avoid short circuiting must be maintained between the wires 10. In other words, a sufficient resistance is maintained between the wires 10, typically about 1 ohm. For convenience in constructing the electrochemical sensor 40, its installation and use, the wires 10 are preferably positioned substantially parallel to one another as is shown in FIGS. 2 and 3. One end of these wires is in contact with a voltage source so which applies a voltage across the wires 10 such that a direct current flows from the second wire through the electrolyte to the first wire.

Since sufficient electrolyte is required at the wires to enable water electrolysis and the migration of the hydrogen ions, as described above, these wires 10 are located in physical contact with the electrically non-conductive conduit 50 and/or the sheath 20. The conduit 50 forms a medium for wicking electrolyte from the electrolyte reservoir plate 70 to the wires 10 and is placed in physical contact with the electrolyte reservoir plate 70. In order to wick electrolyte from the electrolyte reservoir plate 70 to the wires 10, this conduit 50 must be porous. Although a similar or a larger pore size distribution in the conduit 50 as that of the electrolyte reservoir plate 70 can be utilized, a smaller pore size distribution ensures that the conduit 50 will wick and retain electrolyte from the electrolyte reservoir plate 70 due to capillary forces, thereby providing sufficient electrolyte to the wires 10. Possible conduits include: carbides, such as silicon carbide, titanates, such as potassium titanate, aluminates, and mixtures thereof, among others. A silicon carbide which has proven particularly useful with phosphoric acid fuel cells is LONZA® F-360 produced by Lonza Inc., Fairlawn, N.J. LONZA F-360 has a mean particle size of about 20 microns to about 25 microns and forms a mean pore size of about 5 microns to about 15 microns, while the electrolyte reservoir plate in a phosphoric acid fuel cell has a mean pore size of about 10 microns to about 20 microns.

Successfully maintaining sufficient electrolyte in contact with the wires also requires physical contact between the conduit 50 and the wires 10 such that the pore size distribution at the interface between the wires and the conduit 50 does not interfere with the amount of electrolyte in contact with the wires 10. If the pore size distribution at the wire-conduit interface exceeds the pore size distribution of the conduit 50 or if a void exists between the wires 10 and the conduit 50, the conduit 50 may wick the electrolyte away from the wires 10, thereby inhibiting the electrolysis reaction and preventing the operation of the electrochemical sensor. To attain the desired contact between the wires 10 and the conduit 50, and between the electrolyte reservoir plate 70 and the conduit 50, the conduit 50 is preferably used in the form of a pliable paste which can be molded to conform to the shape of the electrolyte reservoir plate 70 and the wires 10. The pliable paste can be formed by adding a liquid compatible with the electrochemical sensor 40 and the fuel cell environment to the conduit 50. For example, phosphoric acid can be added to the silicon carbide for use in a phosphoric acid fuel cell. Assembly can comprise placing the conduit 50 in the electrolyte reservoir plate groove 60, positioning the wires 10 on the conduit 50 so as not to touch each other, and placing additional conduit 50 over the wires 10. Although a rigid conduit rather than a paste can be employed, such an electrochemical sensor is difficult to fabricate and may result in loss of contact between the wires 10 and the conduit 50, and/or the electrolyte reservoir plate 70 and the conduit 50, over time. Therefore, the use of a rigid conduit is less desirable, but is comtemplated by this invention.

When the pliable conduit is employed, it is preferred to utilize a separate, chemically inert, electrically conductive sheath 20 to substantially encapsulate and support the wires since the wire placement in the pliable paste is difficult and impractical. This sheath 20 forms an encasement around the wires 10 to prevent wire to wire contact and to prevent contact between the electrolyte reservoir plate 70 and the wires 10. Possible sheaths 20 include polymer based sheaths, such as fluoro-polymer based sheaths, ceramic based sheaths, polyetheretherketone sheaths, mixtures thereof, and others. Some fluoropolymer sheaths include TEFLON® (polytetrafluoro ethylene) produced by E.I. du Pont de Nemours, E.I. & Company, Wilmington, Del., FLUOREL® produced by 3M Corporation, St. Paul, Minn., fluorinated ethylene propylene, and others. A common ceramic based sheath is alumina. The preferred sheath 20 depends upon the application and operating conditions under which the sheath is to be used. For example, in a molten carbonate fuel cell, where the water electrolysis occurs by a more complex process including the migration of carbonate ions and the production of hydrogen and carbon dioxide at the second wire, a ceramic sheath is preferred due to its high temperature tolerance, while in a phosphoric acid fuel cell, a TEFLON sheath is preferred due to its chemical stability and flexibility.

The dimensions and geometry of the sheath 20 are also application dependent with factors such as wire size and the size of the electrolyte reservoir groove 60, being important. The sheath 20 is preferably sufficiently large to encapsulate, support, and hold the wires 10 stably in the electrolyte containing body groove 60. For example, in a phosphoric acid fuel cell, the sheath 20 can be essentially straight and flexible, having substantially parallel holes running the length of the sheath 20 where the wires 10 are located with dimensions of about 20 centimeters (cm) to about 40 cm in length and about 1.5 mm to about 2.5 mm in width. Another example comprises placing the electrochemical sensor 40 in a frame which surrounds a fuel cell component such that the electrochemical sensor 40 has access to electrolyte. Under such conditions, the electrochemical sensor's dimensions and geometry may be significantly different than when it is located in the electrolyte reservoir plate groove 60, possibly requiring a shorter, thinner sheath 20 and smaller wires 10.

Use of the sheath 20, comprises locating the conduit 50 in an opening 30 of the sheath 20 such that the conduit 50 contacts the wires 10, and when in use, also contacts the electrolyte reservoir plate 70 such that the electrolyte in the electrolyte reservoir plate 70 will be wicked into the conduit 50. The opening 30 of the sheath 20 is preferably sufficiently large such that the amount of wires 10 exposed to the conduit 50 does not limit the rate of the hydrogen producing electrolysis reaction which occurs thereon since the rate of reaction is directly proportional to the amount of wire in contact with the conduit 50. As the amount of contacted wire decreases, the rate of reaction decreases, and the error margin in determining the fuel cell component potential increases. Therefore, it is preferred that the opening 30 be sufficiently large to hold a sufficient amount of the conduit 50 to enable a sufficient amount of electrolyte to be wicked into the conduit 50 to both form an electric circuit between the wires 10 and to have excess water available for the electrolysis reaction. Typically, the opening 30 is located close to the end of the sheath 20 which is inserted into the electrolyte reservoir plate 70, about 0.6 cm to about 5 cm from the end of the sheath 20, with about 1.2 cm to about 4 cm preferred.

The wires 10, which typically protrude from the end of the electrochemical sensor 40 at the end of the sheath 20 furthest from the opening 30, are routed through the anode and cathode chambers of the fuel cell and connected to the voltage source 80 which can be conventional. A voltmeter is additionally connected to the second wire of the electrochemical sensor 40 and to the fuel cell component to be monitored such that the electric potential of the fuel cell component can be measured relative to the second wire.

Advantages of the present invention are readily apparent. With the electrochemical sensor of the present invention, fuel cell component potentials can be determined. This electrochemical sensor can monitor both anode electrode and cathode electrode polarization during cell operation, and anode electrode and cathode electrode voltages, and resistivity during shutdown. Information obtained with the electrochemical sensor can be used as a signal to control the fuel cell and can lead to a better understanding of fuel cells, inefficiencies therewith, and possible solutions and improvements.

Anode electrode polarization establishes the point at which the fuel cell should be shut down to prevent failure due to corrosion (typically prior to the anode reaching oxygen evolution). Anode electrode and cathode electrode voltages can be utilized to control nitrogen purges which maintain low oxygen content in the anode and cathode chambers during transient operating conditions and to prevent anode and cathode electrode damage.

Although this invention has been shown and described with respect to detailed embodiments thereof, it will be understood by those in the art that various changes in form and detail thereof may be made without departing from the spirit and scope of the claimed invention.

We claim:

1. A method for monitoring electrochemical potentials of fuel cell components, comprising:
   a. using an electrochemical sensor having a first electrically conductive wire and a second electrically conductive wire, and a porous, non-conductive conduit in contact with said first wire and said second wire;
   b. contacting said conduit with electrolyte;
   c. wicking said electrolyte to the pores of said conduit;
   d. applying a voltage across said first wire and said second wire;
   e. increasing said voltage until hydrogen evolves from said second wire; and
   f. measuring the potential difference between the fuel cell component and said second wire;

whereby said second wire provides a reference potential and wherein the potential of said second wire is near the open circuit potential of a hydrogen electrode.

2. A method for monitoring electrochemical potentials of fuel cell components as in claim 1 wherein said porous means is a carbide, a titanate, an aluminate, or a mixture thereof.

3. A method for monitoring electrochemical potentials of fuel cell components as in claim 2 wherein said porous means is silicon carbide, potassium titanate, or a mixture thereof.

4. A method for monitoring electrochemical potentials of fuel cell components as in claim 1 wherein said voltage is to about 1.2 volts.

5. A method for monitoring electrochemical potentials of fuel cell components as in claim 1 wherein the fuel cell is an acid fuel cell.

* * * * *